(12) United States Patent
Pfanstiehl

(10) Patent No.: US 8,707,762 B2
(45) Date of Patent: Apr. 29, 2014

(54) LOW COST HUMIDITY AND MOLD INDICATOR FOR BUILDINGS

(76) Inventor: John Gardner Pfanstiehl, Indian Rocks Bch, FL (US)

( * ) Notice: Subject to any disclaimer, the term of this patent is extended or adjusted under 35 U.S.C. 154(b) by 270 days.

(21) Appl. No.: 13/289,445

(22) Filed: Nov. 4, 2011

(65) Prior Publication Data

US 2013/0111976 A1    May 9, 2013

(51) Int. Cl.
G01N 21/81    (2006.01)
(52) U.S. Cl.
USPC .......................................................... 73/29.04
(58) Field of Classification Search
USPC .......................................................... 73/29.04
See application file for complete search history.

(56) References Cited

U.S. PATENT DOCUMENTS

| | | | |
|---|---|---|---|
| 2,017,376 A * | 10/1935 | Rother et al. ..................... | 73/73 |
| 2,249,867 A | 7/1941 | Snelling | |
| 2,716,338 A | 8/1955 | Blinn | |
| 2,951,764 A * | 9/1960 | Chase ............................. | 426/88 |
| 3,085,424 A * | 4/1963 | Berg ............................. | 73/29.02 |
| 3,246,758 A * | 4/1966 | Wagner ......................... | 210/94 |
| 3,425,388 A * | 2/1969 | West ........................ | 73/335.07 |
| 3,680,364 A * | 8/1972 | Carrier ............................. | 73/73 |
| 3,898,172 A | 8/1975 | Reif | |
| 4,150,570 A | 4/1979 | Fuller | |
| 4,723,439 A | 2/1988 | Asakura | |
| 4,793,180 A | 12/1988 | Stewart | |
| 4,990,284 A | 2/1991 | Lauterbach | |
| 5,112,768 A | 5/1992 | Carver | |
| 5,373,738 A | 12/1994 | Abkowitz | |
| 5,922,939 A | 7/1999 | Cota | |
| 6,324,896 B1 | 12/2001 | Aoyagi | |
| 6,663,679 B1 | 12/2003 | Duncan | |
| 6,698,378 B1 | 3/2004 | Dick | |
| 6,798,220 B1 | 9/2004 | Flanigan | |
| 6,877,457 B1 | 4/2005 | Dick | |
| 7,284,412 B1 * | 10/2007 | Perrault ........................... | 73/40 |
| 7,553,450 B2 | 6/2009 | Attar | |
| 7,658,096 B2 | 2/2010 | Pinto | |
| 2002/0130781 A1 * | 9/2002 | Kroll et al. .................... | 340/604 |
| 2006/0272392 A1 * | 12/2006 | Kanare ......................... | 73/29.02 |
| 2007/0266769 A1 * | 11/2007 | Luebbert et al. ............. | 73/29.01 |
| 2009/0035865 A1 | 2/2009 | DeMoor | |
| 2009/0268201 A1 | 10/2009 | Call | |

FOREIGN PATENT DOCUMENTS

JP    2003214927 A  *  7/2003  ............. G01F 23/28

* cited by examiner

*Primary Examiner* — Lisa Caputo
*Assistant Examiner* — Punam Roy

(57) ABSTRACT

A low-cost, easily manufactured humidity and mold indicator for buildings that incorporates a one-piece transparent plastic injection-molded body. Appearance of a warning icon or a change in color alerts the owners or occupants of a building to a hidden leak and thereby prevents costly structural damage, cosmetic damage and mold damage to building components. The indicator is easily inserted and secured into a drilled hole in panel such as a wall or soffit. In one embodiment, the indicator snaps into place after being fully inserted into the panel. In another embodiment, a retainer inserted into the hole holds the indicator enabling easier removal of the indicator for replacement or for inspection of the area behind the panel. An optional removable cap can be painted the same color as the wall. An optional mask covers the integral viewing window during painting of the device.

16 Claims, 3 Drawing Sheets

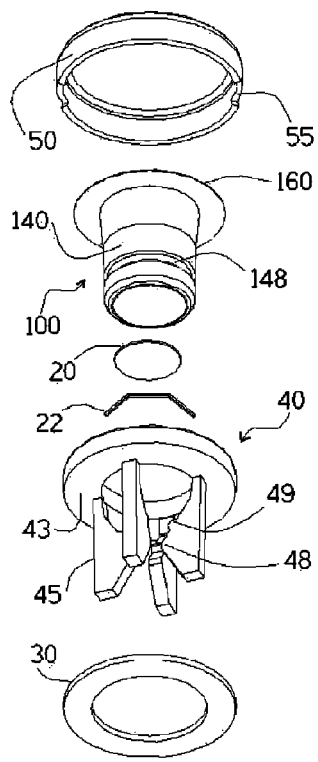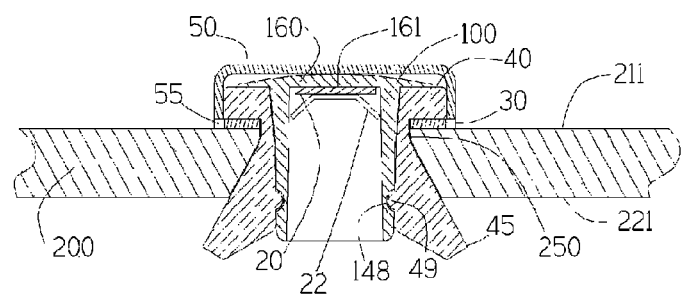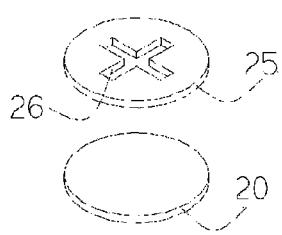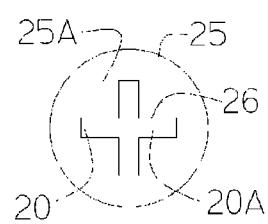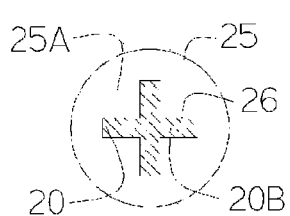
FIG. 5A
FIG. 5B
FIG. 6A
FIG. 6B
FIG. 6C

LOW COST HUMIDITY AND MOLD INDICATOR FOR BUILDINGS

CROSS-REFERENCE TO RELATED APPLICATIONS

Not Applicable

FEDERALLY SPONSORED RESEARCH

Not Applicable

THE NAMES OF THE PARTIES TO A JOINT RESEARCH AGREEMENT

Not Applicable

SEQUENCE LISTING

Not Applicable

FIELD OF THE INVENTION

The present invention relates to devices that provide an external indication of the humidity inside an enclosed space.

BACKGROUND OF THE INVENTION

There is a need for a low cost device to alert building owners and occupants of water leaks and high levels of humidity behind building panels such as behind walls, under floors and above soffits. When these water leaks are not detected quickly, resultant destruction to building components can cost many times the amount of money repairing these leaks would cost if detected early. As a common example, a leak in a roof can, over time, cause rot in the roof deck, rafters, joists, framing, ceilings and soffits. Plumbing leaks also commonly cause similar expensive-to-repair damage to walls, ceilings, studs and flooring.

Water leaks also cause premature corrosion of electrical and other metal components. Additionally, water leaks are the major cause of mold in buildings. Mold has been identified as a major cause of illness, and mold-related costs are estimated in the billions of dollars per year.

These problems are exacerbated by the premature failure of polybutylene piping and connectors, which has resulted in over a billion dollars paid out already through class action law suits in the U.S. It is estimated that six to ten million homes still are plumbed with polybutylene piping and connectors.

No low-cost, easy-to-manufacture humidity indicator device suitable for buildings has been produced or patented. The existing humidity detector devices that use chemicals that change color when predetermined humidity levels are reached were created for industrial shipping containers and sealed cases. By comparison, the present invention is a low-cost, easy-to-manufacture humidity indicator device suitable for residential and commercial buildings U.S. Pat. No. 2,716,338 to Blinn (1955) and U.S. Pat. No. 4,793,180 to Stewart and Blinn (1988) are similar and are representative of current chemical humidity indicator devices.

U.S. Pat. No. 2,716,338, FIG. 1 illustrates closed package 10 with hermetically sealed lid 10a. Device 12 is attached through an aperture. FIG. 3 illustrates the main components of the device, which include button 18 with external threads 19. After the device is inserted through aperture 11, lock nut 14 is screwed on to fasten the device to the closed package 10. Transparent cover 35 is attached to button 18 and covers card 25 which has the chemical.

U.S. Pat. No. 4,793,180 FIG. 1 illustrates similar components. Housing 2 has external threads 11 and is fastened to a sealed container with nut 12. Window 7 covers blotter paper 11 and chemical 18.

The prior art devices have numerous components that are too expensive to manufacture and assemble for widespread use in buildings. The housings of prior art devices are typically metal and require machining of the external threads and other features. The transparent covers or windows require permanent sealing to the housing. By comparison, the present invention has an inexpensive injection-molded one-piece body that does not have threads and does not have a separate window or cover that needs to be permanently fastened and sealed.

The installation of prior art devices into buildings also presents problems. The devices typically are installed using a nut from the inside of the container. This is not possible with buildings because access to the other side of walls, soffits and flooring is often unavailable. Even if the device was installed prior to construction, the nuts prevent future removal. By comparison, the present invention does not require installation of nuts nor does it require access to the inside of the container or wall. The present invention only requires insertion into a drilled hole.

Additionally, removal of the present invention does not require access to the other side of walls, soffits and flooring. The present invention can be easily removed for replacement.

A few prior art devices employ external pipe threads that require internal pipe threads on the container. This cannot work for installation in buildings because typical building materials such as plasterboard and wood are too soft to be threaded. By comparison, the present invention requires no threads in the container or wall and is easily installed in building materials such as plasterboard or wood.

The prior art devices also require a hex head or slots on their housings to tighten the housing or to hold the housing while the nut is tightened. By comparison, the present invention requires no hex head, slots or tools for installation.

In spite of the long felt need for detection of water leaks in buildings, no buildings have inexpensive devices to alert owners and occupants of such leaks behind walls or under roofs. Each year, many millions of dollars will be spent repairing structural damage, mold damage and cosmetic damage to buildings. These damages could have been avoided if a low-cost humidity indicator device was available for installation in buildings. The present invention discloses a novel, easy-to-manufacture device and method that warns people of excessive humidity levels behind panels in buildings.

In spite of active competition among the major corporations that design and manufacture humidity indicator devices, there has been no practical, efficient solution to this problem. The present invention discloses a novel device that solves this problem and satisfies this long felt need.

SUMMARY OF THE INVENTION

The present invention is a low cost humidity and mold indicator for buildings. The objects and advantages of the present invention include:

a) a significant decrease in manufacturing cost due to use of a one piece injection molded body;

b) a significant decrease in manufacturing cost due to elimination of a separate window or cover component;

c) a significant decrease in manufacturing cost due to elimination of the need to permanently attach and seal a separate window or cover component;

d) elimination of the need to machine or mold external threads;

e) elimination of the need for a threaded nut or a threaded panel hole;

f) elimination of the need to access the rear of a building panel to attach the device;

g) ability to install and secure the device from one side of a building panel;

h) ability to easily remove the device from a panel in an assembled building for replacement of the device;

i) ability to easily remove the device from a panel in an assembled building for inspection of the area behind the panel;

j) elimination of the need for a hex head, slots or other means to tighten the device;

k) ability to easily install the device by inserting it into a hole in a building panel; and, l) a warning icon to better alert an owner or occupant of a building to the existence of a hidden leak.

The present invention solves a long felt need in a highly competitive and highly active industry.

Given the long-felt need and large size of the market, it is clear that these improvements have not been obvious in view of the prior art taken as a whole to ones of ordinary skill in this art.

BRIEF DESCRIPTION OF THE DRAWINGS

For a fuller understanding of the nature and the objects of the invention, reference should be made to the following detailed description, taken with the accompanying drawings, in which:

FIG. 5A is a perspective view of a fifth embodiment.

FIG. 5B is a section view of the fifth embodiment installed in a panel.

FIG. 6A is a perspective view of a stencil layer and a blotter paper.

FIG. 6B is a plan view of the stencil with the blotter paper behind it.

FIG. 6C is a plan view of the stencil with the blotter paper behind it with a color change in the blotter paper.

DETAILED DESCRIPTION OF EXEMPLARY EMBODIMENTS OF THE INVENTION

Figures 1A, 1B:
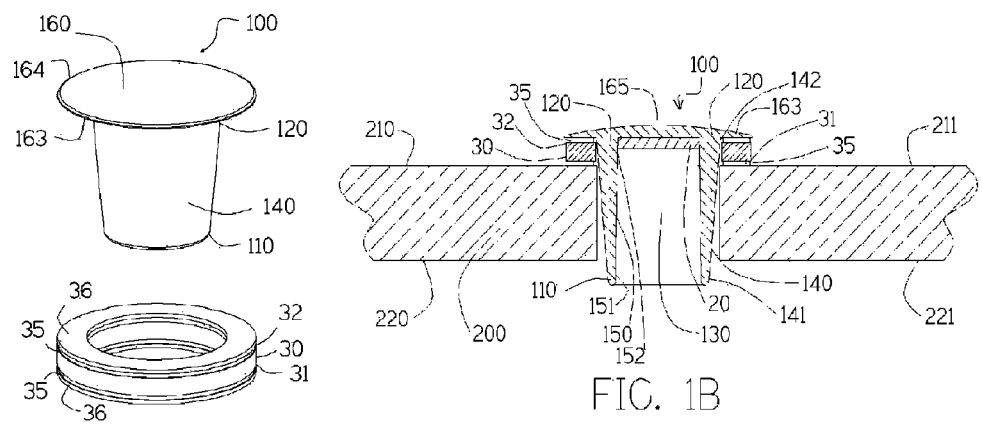
FIG. 1A is a perspective view of a first embodiment.
FIG. 1B is a section view of the first embodiment installed in a panel

FIG. 1A illustrates an exemplary embodiment of the low cost humidity and mold indicator for buildings of the present invention. Body 100 is a one-piece injection-molded transparent plastic elongate hollow cylinder which has a first end 110 that is open and a second closed end 120 that is closed by a disc-shaped closure 160 that hermetically seals closed end 120 creating a humidity detecting chamber inside the body. The periphery 164 of the disc-shaped closure 160 extends beyond the exterior cylindrical surface 140 of the body 100 creating a flange 163.

FIG. 1A also illustrates a gasket 30 that has a first planar surface 31 and a second planar surface 32. An adhesive 35 is on both planar surfaces 31, 32. Tear-off protectors 36 cover the adhesive 35.

FIG. 1B illustrates the embodiment of FIG. 1A installed in a building panel 200, such as a plasterboard wall or a wood soffit. The adhesive 35 on the second planar surface 32 secures and seals gasket 30 to body 100. The adhesive on the first planar surface 31 secures and seals gasket 30 to the exterior surface 211 of the panel 200. A humidity-detecting chamber 130 is open to the air behind the interior side 220 of the panel 200 but is sealed off from the air on the exterior side 210 of the panel 200 by the gasket 30.

A humidity sensitive chemical 20 changes color when a predetermined relative humidity level on the interior side 220 of the panel 200 is exceeded. The color change is visible from the exterior side 210 of the panel 200 through transparent lens 165, which is an integral part of the body 100.

One conventional humidity sensitive chemical is cobalt chloride which is blue when the relative humidity it is exposed to is less than a predetermined relative humidity level. Cobalt chloride changes color from blue to pink when the relative humidity it is exposed to is greater than a predetermined relative humidity level. The color change is reversible. Cobalt chloride changes back to blue when the relative humidity it is exposed to returns to less than a predetermined relative humidity level. Cobalt-free humidity sensitive chemicals are also usable. For example, copper chloride changes color from azure to brown depending on the relative humidity it is exposed to.

Another group of humidity sensitive chemicals that can be employed in the present invention changes irreversibly when the relative humidity it is exposed to is greater than a predetermined relative humidity level. One example of this group dissolves from a crystalline form creating an identifiable blue spot. Another group of humidity sensitive chemicals that can be employed in the present invention changes color irreversibly when exposed to liquid water. Examples of this group can be found in some cell phones, and they change from white to red or from white to blue.

Exterior cylindrical surface 140 has a diameter 141 at the open end 110 that is smaller than the diameter 142 at the closed end 120 forming an exterior draft angle that enables easy removal of the body 100 from an injection mold (not shown). Interior cylindrical surface 150 has a diameter 151 at the open end 110 that is larger than the diameter 152 at the closed end 120 forming an interior draft angle that enables easy removal of the body 100 from an injection mold.

Flange 163 limits the insertion of the body 100 into the hole in panel 200.

Figures 2A, 2B:
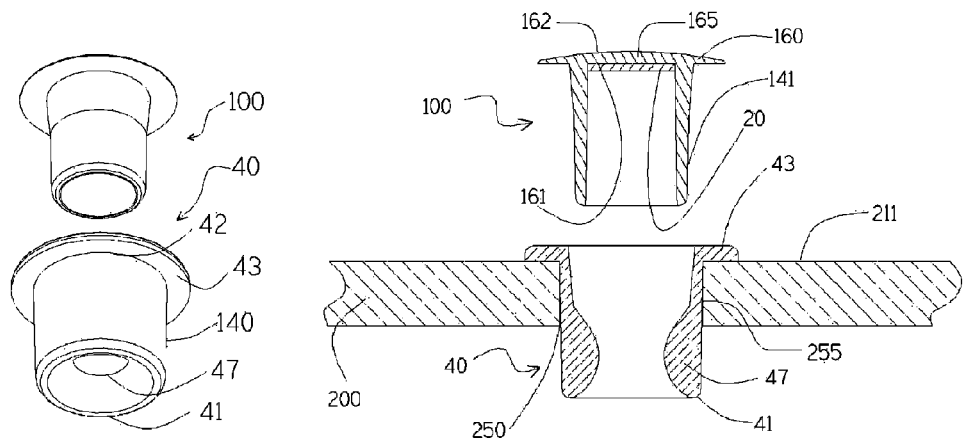
FIG. 2A is a perspective view of a second embodiment.
FIG. 2B is a section view of the second embodiment partially installed in a panel.
Figure 2C:
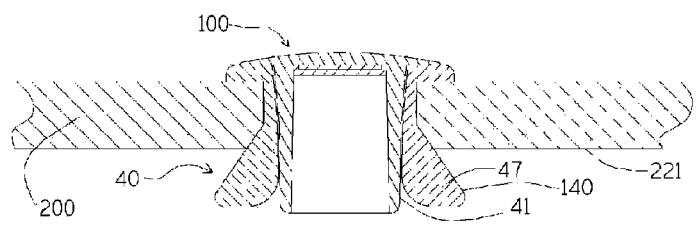
FIG. 2C is a section view of the second embodiment completely installed in a panel.

FIG. 2A illustrates a second embodiment of the present invention. Soft plastic retainer 40 is a hollow elongate cylinder with an integral flange 43 that contacts the exterior panel surface 211 when the retainer 40 is inserted into a hole 250 in the panel 200 as illustrated by FIG. 2B. Body 100 is inserted into the retainer 40 after the retainer 40 is in the panel 200. The wall thickness 47 of the retainer 40 at its first end 41 is greater than the difference between the diameter 255 of the hole 250 and the exterior diameter 141 of the body 100. FIG. 2C illustrates the exterior surface 140 of the retainer 40 forced outward against the interior surface 221 of the panel 200 when the body 100 is inserted, thereby securing and sealing the body 100 in the panel 200.

FIG. 2B also illustrates the exterior surface 162 and interior surface 161 of the disc-shaped closure 160 create a convex lens 165 to magnify viewing of chemical 20.

Figure 3A:
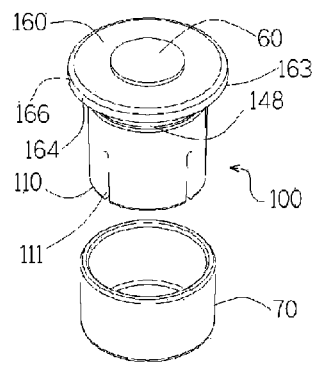
FIG. 3A is a perspective view of a third embodiment.

FIG. 3A illustrates a third embodiment of the present invention. A disposable seal 70 slides over the first end 110 of the body 100 to prevent ambient humidity from changing the chemical 20 during storage and transport. The seal 70 is configured to be larger than the hole 250 in the panel 200 to make certain the installer removes the seal 70 before installation of body 100 into the panel 200.

Mask 60 prevents paint from coating the entire exterior surface 162 if housing 100 is painted. The mask 60 is removed and disposed after painting or after installation.

Figure 3B:
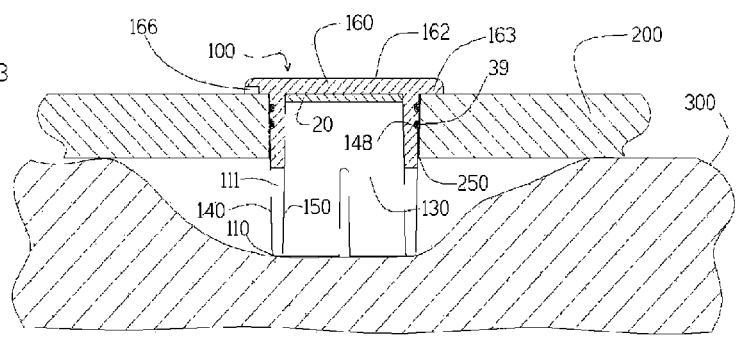
FIG. 3B is a section view of the third embodiment installed in a panel.

Ventilation openings illustrated by ventilation slots 111 extend between the external cylindrical surface 140 to the internal cylindrical surface 150 of the body 100 adding another path for air to reach the humidity chamber 130. FIG. 3B illustrates body 100 installed in a panel 200. Insulation 300 or other building materials that contact or block open end 110 of the body 100 cannot seal off the humidity chamber 130 because air can travel through the ventilation slots 111 also.

Grooves 148 aid in the retention of caulk 39, which is used to seal and secure the housing 100 in the panel 200.

Indentation 166 in the periphery 164 of the disc-shaped closure 160 of the body 100 permits partial insertion of a small flat-blade tool (not shown) to pry under the flange 163 of the body 100 to remove the body 100 if desired at a later time.

Figure 4A:
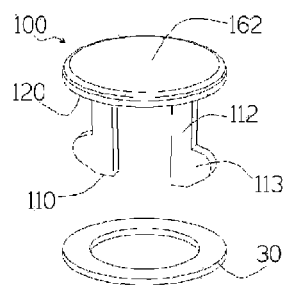
FIG. 4A is a perspective view of a fourth embodiment.

FIG. 4A illustrates a fourth embodiment of the present invention. Fingers 112 are attached at the closed end 120 of body 100 and are able to flex radially inward at the open end 110 of the body 100.

Figure 4B:
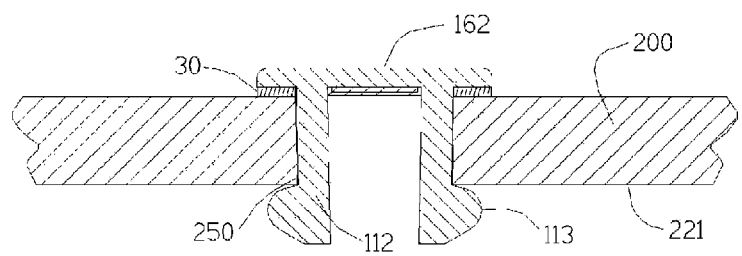
FIG. 4B is a section view of the fourth embodiment installed in a panel.

FIG. 4B illustrates the body 100 installed in a panel 200. Protrusions 113 extend radially outward to a radius greater than the radius of the panel hole 250. The protrusions 113 are forced inward they are inserted into the hole 250 and spring back out as they exit the hole 250 on the interior side 221 of the panel 200. This secures the body 100 in the panel 200. Dimensions of the fingers 112 and the gasket 30 are selected so that the gasket 30 is compressed and the body 100 is well secured in a building panel 100 of a standard thickness.

FIG. 5A illustrates major components of a fifth embodiment of the present invention. FIG. 5B illustrates the present invention installed into a panel 200. During installation, retainer 40 is inserted into gasket 30. Next the retainer 40 is inserted into the panel 200. Body 100 is then inserted into the retainer 40, and finally optional cap 50 is installed if desired.

Retainer 40 has a number of fingers 45 that are flexibly attached near flange 43. Protrusions 48 on each finger 45 extend radially inward to a radius less than the radius of the external cylindrical surface 140 of the housing 100. Insertion of the body 100 forces the fingers 45 outward into the panel hole 250 and thereby secures both the retainer 40 and the body 100 to the panel 100. The fingers 45 are configured to work with a range of thickness of common building panels.

Nipple 49 extends further inward from the finger 45. When the body 100 is fully inserted into the retainer 40, the nipple 49 snaps into groove 148 on the exterior cylindrical surface 140 of the body 100 to lock or latch the body 100 in that position. This illustrates one latch means that locks body 100 to the retainer 45 when the body 100 is fully inserted into the retainer 45.

Cap 50 can be painted the same color as the exterior surface 211 of the panel 200 and installed on the body 100 or on the retainer 40 to make the present invention less visually intrusive. The cap 50 can be removed whenever desired to see if the chemical 20 indicates excessive humidity or mold.

Indentation 55 facilitates removal of cap 50 when desired. A small flat blade tool (not shown) can be inserted into the indentation 55 to help remove the body 100 by prying it off.

Chemical 20 can be absorbed by a porous material such as blotter paper. Support 22 illustrates a spring clip as one means for holding the chemical 20 to the interior surface 161 of the disc-shaped closure 160 of the body 100. Other support means can include hollow cylinders, adhesives and porous materials such as cotton packing.

FIG. 6A illustrates a chemical layer 20 such as blotter paper. Stencil 25 is an opaque non-porous material with a stencil cutout 26. The shape of the cutout 26 can be a recognizable warning icon such as an "X." The color of the stencil 25 is the same as the color of the chemical layer when humidity is below the predetermined level, typically blue.

FIG. 6B illustrates how the stencil 25 and chemical layer 20 appear when the relative humidity is below the predetermined value. Both the color 25A of the stencil 25 and the color 20A of underlying chemical layer 20 are the same color and therefore the "X" would be barely visible. FIG. 6C illustrates how the colors 20A, 25A appear when relative humidity is above the predetermined value. Now the color 20B of underlying chemical layer 20 is a different color, commonly red, than the color 25A of the stencil 25 and thereby the warning icon appears as a red "X" through a blue foreground. Therefore the homeowner or occupant does not need to know or remember what color the indicator displays when there is a hidden leak. Appearance of the warning icon signals the problem.

This invention is clearly new and useful. Moreover, it was not obvious to those of ordinary skill in this art at the time it was made in any of the highly competitive industries active in this art.

It will thus be seen that the objects set forth above, and those made apparent from the foregoing description, are efficiently attended. Since certain changes may be made in the foregoing construction without departing from the scope of the invention, it is intended that all matters contained in the foregoing construction or shown in the accompanying drawings shall be interpreted as illustrative and not in a limiting sense.

It is also understood that the following claims are intended to cover all of the generic and specific features of the invention herein described, and all statements of the scope of the invention which, as a matter of language, might be said to fall there between.

What is claimed is:

1. An easily manufactured device for indicating water leaks or mold formation behind a building panel such as a wall, a floor or a soffit by providing a visual alert when a predetermined relative humidity level is exceeded, the device comprising:

a) a one-piece injection molded transparent plastic elongate hollow cylindrical body, said body having
      a first end that is open;
      a second end that is closed;
      an exterior cylindrical surface including a diameter of said exterior cylindrical surface being smaller at said open end than at said closed end to form an exterior draft angle enabling easy removal from an injection mold;
      an interior cylindrical surface including a diameter of said interior cylindrical surface being larger at said open end than at said closed end to form an interior draft angle enabling easy removal from an injection mold;

a disc-shaped closure disposed on said closed end including an exterior surface, an interior surface, and a periphery, wherein said disc-shaped closure hermetically seals said closed end of said body creating a humidity detecting chamber inside said body, and wherein said periphery of said disc-shaped closure outwardly extends from said exterior surface of said body creating a flange configured to limit the insertion of said body into a hole in said panel;

b) a humidity sensitive chemical that is
a first color when exposed to relative humidity that is less than a predetermined relative humidity level and that is a second color when exposed to relative humidity that is greater than said predetermined relative humidity level, said chemical disposed in proximity to said interior surface of said disc-shaped closure inside said humidity detecting chamber, wherein said open end of said device is inserted into said hole in said panel to expose said humidity detecting chamber to the air behind said panel whereby a color change visible through
said disc-shaped closure on the exterior side of said panel indicates the possibility of water leaks or mold formation on the interior side of said panel and c) an elongate one-piece plastic retainer that is inserted into said hole in said panel,
said retainer having a first end and a second end, said first end configured to be inserted into said hole, said second end having a flange larger than said hole wherein said flange abuts said panel when said first end is inserted into said hole, said first end further configured to expand when said body is inserted into said retainer whereby said retainer and said body are fixably attached inside said hole.

2. The device of claim 1 wherein said retainer is further comprised of:
a hollow cylindrical soft plastic body with a first end that is open, a second end that is open, an average wall thickness at said first end that is greater than one half the difference in diameter of said hole and the outside diameter of said exterior cylindrical surface at said first end of said body, whereby the first end of said retainer is forced to expand outwardly when said body is inserted into said retainer and said retainer and said body are thereby fixably attached inside said hole.

3. The device of claim 1 wherein said retainer is further comprised of:
a hollow plastic body with a first end that is open, a second end that is open, a plurality of fingers extending longitudinally from said second end to said first end, said fingers being flexibly attached near said second end permitting radial movement of said fingers, said fingers configured to permit insertion of said retainer into said hole, and said fingers further configured to expand outwardly when said body is inserted into said retainer wherein said retainer and said body are fixably attached inside said hole.

4. The device of claim 3 further comprising:
a latch on said fingers configured to provide resistance to withdrawal of said body from said retainer when said body is fully inserted into said retainer.

5. The device of claim 1 further comprising:
a flexible gasket configured to hermetically seal said body to said panel, said gasket having a first surface that contacts said panel and a second surface that contacts said body.

6. The device of claim 5 further comprising:
an adhesive on said first surface that contacts said panel; and
an adhesive on said second surface that contacts said body whereby said gasket fixably attaches said body to said panel.

7. The device of claim 1 further comprising:
a cap configured to be releasably attached to said device on said panel whereby said device is covered from view and a user is provided the option to paint said cap the same color as said panel.

8. The device of claim 7 further comprising:
an indentation on said cap that is configured to allow a small tool to be inserted into said indentation to pry said cap from said device.

9. The device of claim 1 further comprising:
an indentation on said flange that is configured to allow a small tool to be inserted into said indentation to pry said body from said panel.

10. The device of claim 1 further comprising:
a blotter paper containing said humidity sensitive chemical; and
a support configured to slide into said humidity detecting chamber and hold said blotter paper in proximity to said disc-shaped closure and
a non-absorbent stencil layer of said first color, said stencil layer having a cutout in the shape of a warning icon, wherein said blotter paper and said stencil layer are the same color when exposed to relative humidity that is less than said predetermined relative humidity level and wherein said warning icon appears as said second color when said humidity sensitive chemical is exposed to a relative humidity that is greater than said predetermined relative humidity level.

11. The device of claim 1 further comprising:
a disposable seal configured to hermetically seal said humidity detecting chamber.

12. The device of claim 1 further comprising:
a plurality of ventilation openings disposed on said body at said first end whereby said humidity detecting chamber is open to air behind said panel when said first end contacts a layer of insulation or another building material.

13. The device of claim 1 further comprising:
a mask releasably attached to said exterior surface of said disc-shaped closure.

14. An easily manufactured device for detecting water leaks or mold formation behind a panel such as a wall, a floor or a soffit by providing a visual alert when a predetermined relative humidity level is exceeded, the device comprising:
a) a one-piece injection molded transparent plastic elongate hollow cylindrical body, said body having
a first end that is open;
a second end that is closed;
an exterior cylindrical surface including a diameter of said exterior cylindrical surface being smaller at said open end than at said closed end to form an exterior draft angle enabling easy removal from an injection mold;
an interior cylindrical surface including a diameter of said interior cylindrical surface being larger at said open end than at said closed end to form an interior draft angle enabling easy removal from an injection mold;
a disc-shaped closure disposed on said closed end including an exterior surface, an interior surface, and a periphery, wherein said disc-shaped closure hermetically seals said closed end of said body creating a humidity detecting chamber inside said body, and wherein said periphery of said disc-shaped closure outwardly extends from said exterior surface of said body creating a flange configured to limit the insertion of said body into a hole in said panel;

a plurality of fingers extending longitudinally from said second end, wherein said fingers are flexibly attached near said second end permitting radial movement of the ends of said fingers, said fingers further comprising radially outwardly extending protrusions near said ends of said fingers wherein said fingers are configured to move radially inwardly as said body is inserted in said hole and said fingers are configured to move radially outwardly beyond the diameter of said hole as said body is fully inserted into said hole, whereby said body is fixably attached inside said hole;

b) a humidity sensitive chemical that changes color when said predetermined relative humidity level is exceeded disposed in proximity to said interior surface of said disc-shaped closure inside said detecting chamber, wherein said open end of said device is inserted into said hole in said wall to expose said humidity chamber to the air behind said panel whereby a color change visible through said disc-shaped closure on the exterior side of said panel indicates the possibility of water leaks or mold formation on the interior side of said panel; and c) a flexible gasket configured to hermetically seal said body to said panel.

15. The device of claim 14 further comprising:
a cap configured to be releasably attached to said device on said panel whereby said device is covered from view and a user is provided the option to paint said cap the same color as said panel, said cap further comprising an indentation that is configured to allow a small tool to be inserted into said indention to pry said cap from said device.

16. A method for using an easily manufactured device to indicate water leaks or mold formation behind a panel such as a wall, a floor or a soffit by providing a visual alert when a predetermined relative humidity level is exceeded, the method comprising the steps of:
 a. Drilling a hole in said panel;
 b. Providing a retainer configured to be inserted into said hole;
 c. Inserting said retainer into said hole;
 d. Providing a one-piece injection molded transparent plastic elongate hollow cylindrical body having a first end that is closed, a second end that is open, and a humidity sensitive chemical that changes color when said predetermined relative humidity level is exceeded;
 e. Providing a flexible gasket configured to hermetically seal said body to said panel;
 f. Inserting said body into said gasket;
 g. Inserting said body into said retainer; and
 h. Observing said humidity sensitive chemical to detect a color change that indicates that said predetermined relative humidity level is exceeded.

* * * * *